United States Patent [19]
Widlund et al.

[11] Patent Number: 5,702,378
[45] Date of Patent: Dec. 30, 1997

[54] RESILIENT MATERIAL AND DISPOSABLE, ABSORBENT ARTICLE COMPRISING SUCH A MATERIAL

[75] Inventors: Urban Widlund, Mölnlycke; Roy Hansson, Mölndal, both of Sweden

[73] Assignee: Mölnlycke AB, Göteborg, Sweden

[21] Appl. No.: 447,531

[22] Filed: May 24, 1995

Related U.S. Application Data

[62] Division of Ser. No. 781,141, filed as PCT/SE90/00475, Jul. 3, 1990, published as WO91/00720, Jan. 24, 1991, Pat. No. 5,486,273.

[30] Foreign Application Priority Data

Jul. 6, 1989 [SE] Sweden ............... 8902457

[51] Int. Cl.⁶ ............................................. A61F 13/15
[52] U.S. Cl. ...................... 604/373; 604/383; 604/385.2
[58] Field of Search ............................. 604/383, 385.2, 604/373, 385.1, 370, 386.1, 380, 378, 384

[56] References Cited

U.S. PATENT DOCUMENTS

| | | | |
|---|---|---|---|
| 4,184,902 | 1/1980 | Karami | 604/383 |
| 4,342,314 | 8/1982 | Rodel et al. | 604/370 |
| 4,692,163 | 9/1987 | Widlund et al. | 604/385 |
| 5,188,625 | 2/1993 | Van Iten et al. | 604/383 |

FOREIGN PATENT DOCUMENTS

| | | |
|---|---|---|
| 0 098 983 | 1/1984 | European Pat. Off. . |
| 0 195 113 | 9/1986 | European Pat. Off. . |
| 0 203 820 | 12/1986 | European Pat. Off. . |
| 0 302 611 | 2/1989 | European Pat. Off. . |
| 8406071-4 | 6/1987 | Sweden . |
| 1 253 664 | 2/1971 | United Kingdom . |
| 2 218 990 | 11/1989 | United Kingdom . |

*Primary Examiner*—John G. Weiss
*Assistant Examiner*—David J. Cho
*Attorney, Agent, or Firm*—Burns, Doane, Swecker & Mathis, L.L.P.

[57] ABSTRACT

A disposable, absorbent article such as a diaper or an incontinence guard includes an absorbent pad disposed between inner and outer casing layers. At least one of the inner and outer casing layers is made of an elastic material having areas from which material has been removed while leaving coherent material parts in order to impart different elastic properties to different parts of the material. The material removed can be in the form of through holes or blind holes.

3 Claims, 3 Drawing Sheets

RESILIENT MATERIAL AND DISPOSABLE, ABSORBENT ARTICLE COMPRISING SUCH A MATERIAL

This application is a divisional of application Ser. No. 07/781,141, filed as PCT/SE90/00475, Jul. 3, 1990 published as WO91/00720, Jan. 24, 1991 now U.S. Pat. No. 5,486,273.

BACKGROUND OF THE INVENTION

1. Field of the Invention

The present invention relates to a method of imparting varying degrees of elasticity or springiness to different areas of thin resilient material, preferably the casing or enveloping material of absorbent, disposable articles, such as disposable diapers and incontinence guards. The invention also relates to a material manufactured in accordance with this method, and an absorbent, disposable article in which such a material is used as casing material.

It has become progressively more usual to provide disposable, absorbent articles of the aforesaid kind with elastication with the intention of improving the reliability of said articles against leakage and also to adapt the shape of such articles to the body shape of the wearer. This elastication often comprises elastic threads or filaments attached to a casing layer of the article and forming leg and waist elastic. It is also known to form waist elastic from thermoplastic material having a so-called elastic memory, instead of using elastic threads. The elastic properties of such material are enhanced, by stretching said material to the region of its plasticity range and thereby obtain a larger size. When the material is subsequently heated, the material shrinks to its original size and becomes elastic, so that it can be stretched resiliently to its earlier stretched state. Such memory materials afford technical advantages in manufacture in comparison with elastic threads, since it is necessary to hold such threads stretched during all the manufacturing stages of the article, whereas the elasticity of the memory material is obtained by heating the material after the article has been manufactured.

It is also known to use elastication for the purpose of imparting to the absorbent pad of an absorbent disposable article of the aforesaid kind a shape which will enable the article to be placed in position on the wearer more readily and which will improve the function of the article. Reference is made in this respect, for instance, to Swedish Patent Specification No. 8406071-4, which relates to such an article in which elastic threads are disposed in the form of a network, such as to form a pattern having curved parts, for instance curved leg elastic.

2. Description of the Related Art

Furthermore, it is known from EP 0 098 983 to provide a diaper with resilient casing material surrounding the absorbent pad or body, such as to provide waist and leg elastic. In the case of this diaper, the resilient material is not prestretched, which means that it is necessary to produce all of the elastic force when putting on the article. Consequently, when using casing material of this kind it is not possible to deform the absorbent pad of a diaper in order to improve diaper function.

Despite long-term efforts by diaper manufacturers to provide improved shape-adaptability and improved leakage reliability with the aid of elastication, no manufacturer has successfully produced disposable, absorbent articles of the aforesaid kind which measure up to the hitherto best solution in these respects, namely diapers which are held on the child wearer with the aid of resilient pants provided with waist and leg elastication and particularly configured for the purpose intended.

OBJECTS AND SUMMARY

The present invention relates primarily to a method by which different areas on parts of a sheet of resilient material can be readily given varying degrees of elasticity such as to enable the material to be adapted optimally to the functional requirements of the casing material which embraces the absorbent body of a disposable, absorbent article of the aforesaid kind. The inventive method can, of course, also be applied in other instances where a resilient material is required to exhibit varying degress of elasticity in different areas thereof.

This object is achieved in accordance with the invention by removing material from those parts or areas of the resilient material which are to be given a lower degree of elasticity than remaining areas or parts of said material, while leaving attached material parts in those areas from which material has been removed. The method enables selective patterns of removed material areas to be readily achieved. The method also enables the casing material of disposable articles of the aforesaid kind to be readily produced and with good precision with a desired elastic pattern with varying degrees of elasticity in different areas of the pattern.

The invention also relates to material manufactured in accordance with the method, and to a disposable, absorbent article whose casing material comprises such resilient material.

In accordance with one preferred application of the inventive method for the manufacture of disposable, absorbent articles of the aforesaid kind, the resilient material consists of a so-called memory material which is heated after the manufacture of the remainder of the article has been completed.

BRIEF DESCRIPTION OF THE DRAWINGS

An exemplifying embodiment of the invention will now be described in more detail with reference to the accompanying drawings, in which.

DETAILED DESCRIPTION OF THE PREFERRED EMBODIMENTS

Figure 1:
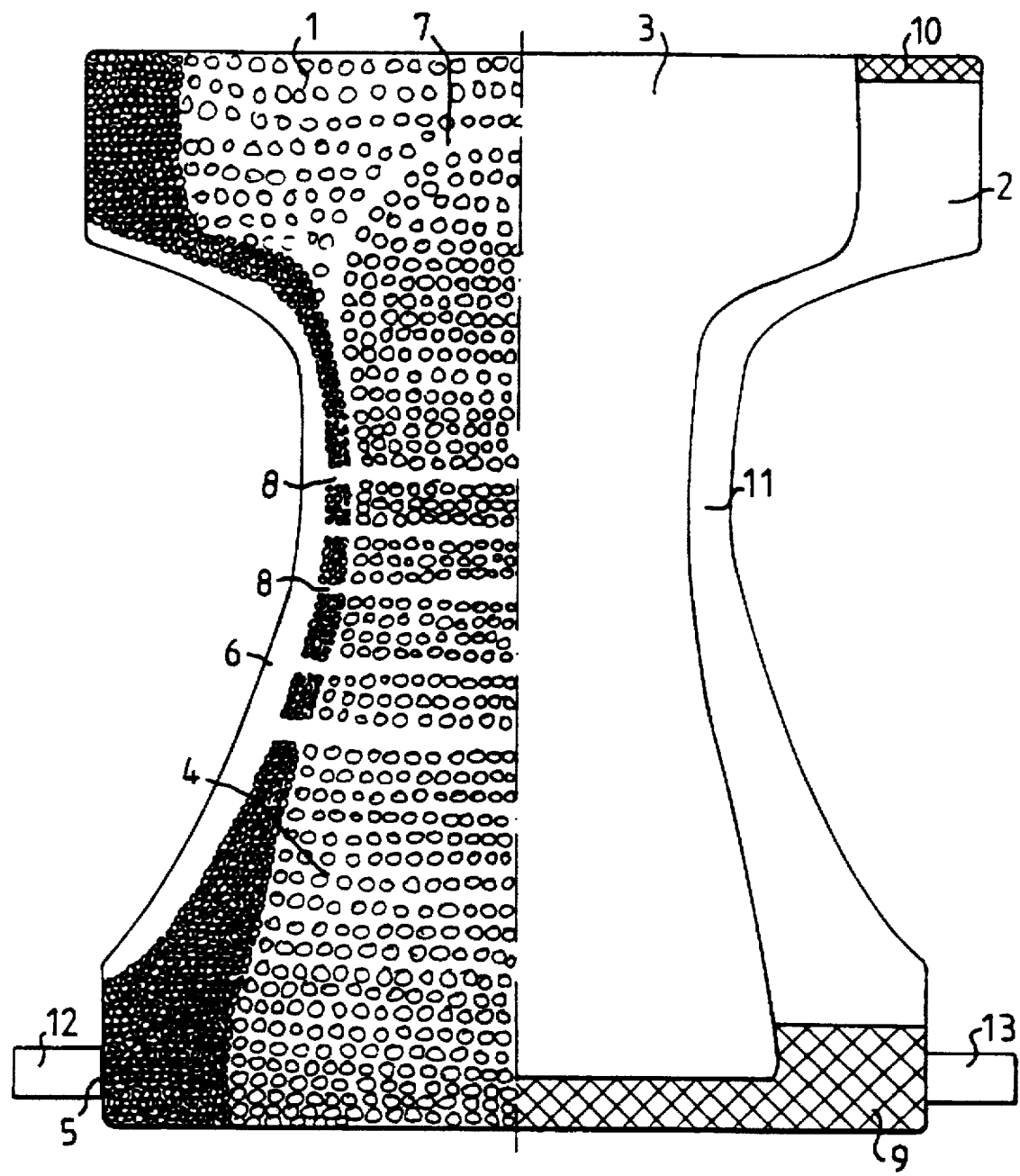
FIG. 1 illustrates a diaper which includes casing material manufactured in accordance with the inventive method.

FIG. 1 illustrates a diaper and shows the side of the diaper which is intended to lie closest to the wearer in use. The diaper is constructed in a conventional manner from an inner and an outer casing material 1 and 2 respectively, and a T-shaped absorbent pad 3 located therebetween.

The inner casing material 1 includes a pattern of through-passing and blind holes 4 and 5 respectively, which have been formed in the casing material 1 in a manner and with the aid of means hereinafter described. The through-passing holes 4 are disposed on that part of the casing material i which extends over the absorbent pad 3, whereas the blind holes 5 are disposed on those parts of the casing material 1 which form side flaps externally of the absorbent pad. The casing material 1 also includes imperforate parts 6, 7, 8, i.e. parts from which no material has been removed.

The back and front ends of the outer casing material 2 include imperforate parts 9 and 10 respectively from which no material has been removed and which, in the FIG. 1 embodiment, are indicated by mutually intersecting lines, and an intermediate part 11 in which blind holes have been formed.

Attached, in a conventional manner, to the back end of the diaper are two side-fastener tabs 12, 13 by means of which the sides of the front and back parts of the diaper can be joined together, to give the diaper a pants-like configuration.

The resilient materials forming the casing material of a disposable diaper and provided with the aforedescribed pattern, in accordance with the inventive method, preferably consist of mutually the same or mutually different thermoplastic materials of the "memory type". Subsequent to being heated, such material will contract to its original size while remaining elastically stretchable from its contracted state to an extended or stretched state. A suitable material in this respect is, for instance, EXAFLEX, which is marketed by the company Exxon.

The method of forming the through-passing and blind holes in the casing materials 1 and 2 will now be described with reference to FIGS. 2-4.

Figure 2:
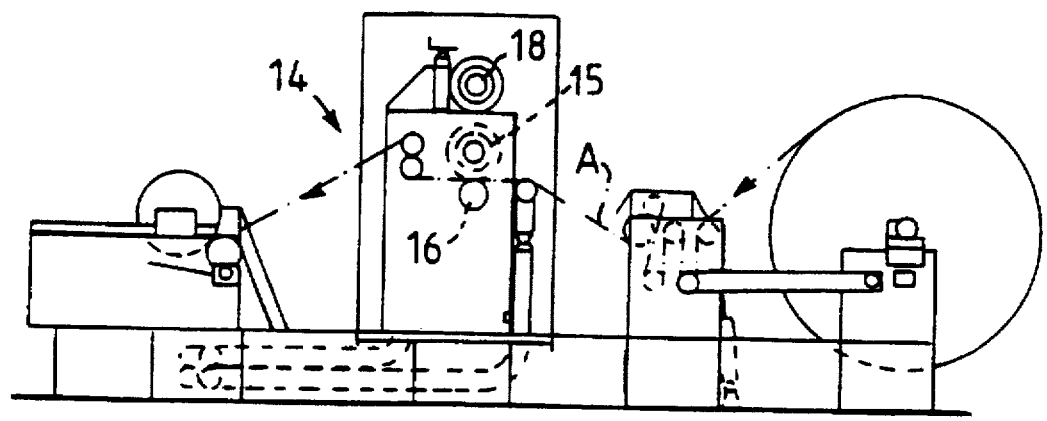
FIG. 2 illustrate schematically an exemplifying embodiment of apparatus for removing material from a material web.
Figure 3:
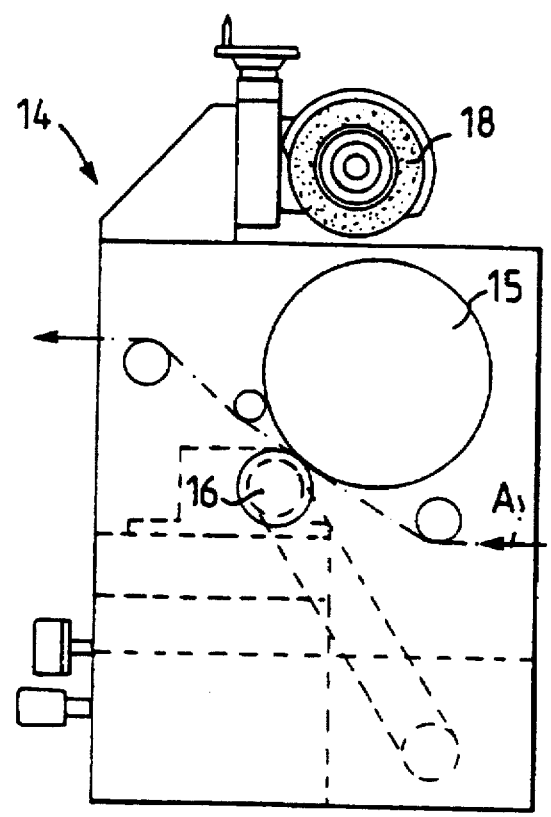
FIG. 3 is an enlarged view of the apparatus of FIG. 2.
Figure 4:
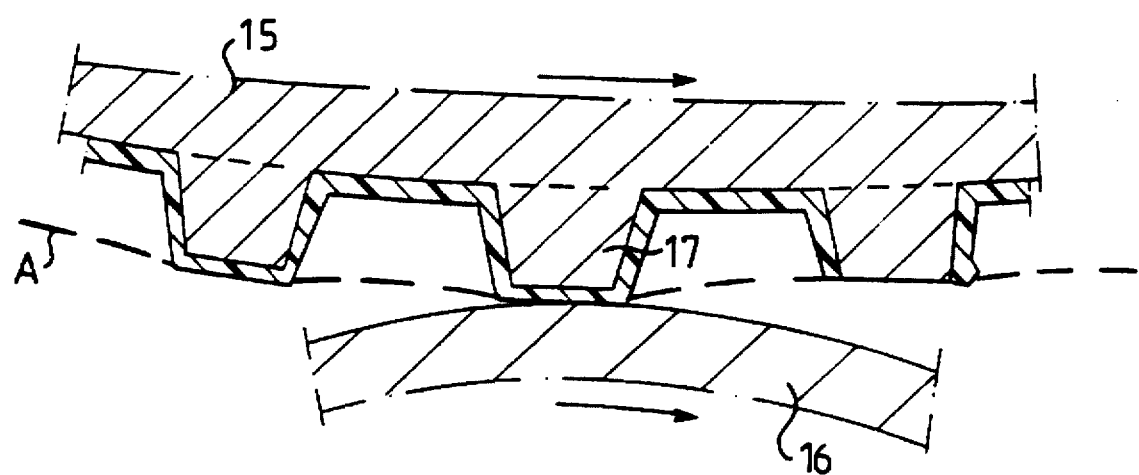
FIG. 4 is an enlarged view of a tool cylinder and milling cylinder used in the apparatus of FIGS. 2 and 3.

FIGS. 2-4 illustrate schematically a machine unit 14 which functions to form holes in material and for thinning material in a controlled fashion, i.e. a so-called perforating unit, which may be a converted, commercially available machine unit originally intended for perforating sheets of postage stamps or sheets of labels.

The perforating unit 14 includes a tool cylinder 15 and a milling cylinder 16 which coacts with the tool cylinder 15. A material web A, which is to be perforated or in which holes are to be formed, is passed between the two cylinders 15 and 16. The tool cylinder 15 is provided with outwardly projecting knife-elements 17 which function to remove material from the web A, as shown in FIG. 4. The perforating unit also includes means (not shown) which enable the distance between the rotational axes of the tool cylinder 15 and the milling cylinder 16 to be accurately adjusted, so that in the working position the knife-elements 17 can be located at a distance from the peripheral surface of the milling cylinder and therewith thin the material web A solely by removing material therefrom.

When the knife-elements 17 occupy the position illustrated in FIG. 4, the knives will form through passing holes in the web A. It will be understood that the tool cylinder can be provided with knife-elements of mutually different height, so as to produce through-passing holes and blind holes at the same time.

The perforating unit 14 also includes grinding equipment 18 for sharpening the knife-elements 17, means for advancing the web A through the unit 14, and means for driving the tool cylinder and milling cylinder respectively.

In the case of the illustrated preferred embodiment, the knife-elements 17 are configured to produce circular through-passing and blind holes in the pattern illustrated in FIG. 1. The knife-elements may, of course, be given another configuration, for instance a rectangular configuration. If it is desired to produce coherent areas from which of web material has been removed larger than those that can be produced by means of a single pair of tool and milling cylinders, the perforating unit can be provided with several such pairs and said pairs arranged to produce mutually over-lapping patterns of removed web-parts.

Thus, desired patterns of areas in which material is removed can be achieved by appropriate design of the perforating unit.

When the resilient material is not a memory material, but a conventional resilient material and the perforating unit or units is, or are, installed in the diaper manufacturing line, the perforating units may conveniently be provided with means which enable the resilient material to be fed through a respective perforating unit in a pre-tensioned, i.e., stretched, state.

In accordance with one advantageous variant of the invention, the inner casing material 1, and therewith the aforedescribed material web A, may consist of a two-ply material comprising a laminate of resilient material and non-woven material.

In the manufacture of the diaper illustrated in FIG. 1, the casing materials are advantageously fed through a conventional diaper manufacturing line in a stretched state, i.e. prior to the final heating stage in which said materials strive to return to their original dimensions. The final heating of the respective casing materials is thus effected subsequent to having joined together those parts of the inner and outer casing materials which lie externally of the absorbent pad, said material parts preferably being glued together.

This avoids the complication that constantly manifests in manufacture when using conventional casing materials which incorporate elastic elements, namely that these elements, for instance elastic threads, must be held stretched during the manufacture of said diapers.

The diaper illustrated in FIG. 1 has not yet been subjected to said final heating stage. Thus, when the diaper illustrated in FIG. 1 is heated, the casing materials 1 and 2 will strive to return to their original size. However, this reduction in size of the casing materials is counteracted by the relatively rigid absorbent pad 3, this counteraction being of a greater or lesser degree due to varying degrees of elasticity in different parts of the casing materials. In the illustrated embodiment, the elastic force in the parts 7 and 8 of the inner casing material are sufficiently great to deform the absorbent body and therewith generate a basin-like shape within the region of the part 7 and a 20, gutter-like shape in the region of the part 8. The elastic forces in the parts 9 and 10 of the outer casing material are sufficiently great to compress the absorbent pad slightly in its transverse direction. The elastic forces in remaining parts lying inwardly of the absorbent body are too small for the casing materials to be able to shrink in size against the influence exerted by the rigidity of the absorbent pad. However, the endeavors of the memory material to return to its original size ensures that no folds are formed in the casing materials in conjunction with the deformation of the absorbent pad caused by the material parts 7-10.

The absorbent pad also influences the reduction in size of external casing parts located nearest said pad, these parts being joined together in a conventional fashion, by preventing contraction of said parts, particularly in their longitudinal direction. The outer casing parts, however, are able to contract without hinder from the absorbent pad.

Thus, it is possible by means of the present invention to produce an all-in-one diaper incorporating waist and leg elastic of the same quality as the elastic pants normally used to hold diapers against the body of the wearer, and comprising casing material which resiliently urges the absorbent pad against the body of said wearer. Furthermore, the configuration of the casing material of the diaper illustrated in FIG. 1 will also cause the absorbent pad to adopt a basin-like shape in the region of the wetting point and a gutter-like shape in the crotch region of the diaper when worn, these configurations being beneficial with respect to the absorption capacity and leakage reliability of the diaper.

The described, exemplifying embodiment should be seen solely as a non-restrictive example of how a resilient material can be configured in accordance with the invention. It will be understood that many variants are conceivable to one skilled in this art, particularly with respect to the selected pattern and material combinations. This also applies to the illustrated application of the inventive casing material. For instance, the outer casing material may be provided with conventional waist elastic and solely the inner casing material may comprise an inventive resilient material. The scope of the invention is therefore restricted solely by the scope of the following claims.

We claim:

1. A disposable, absorbent article such as a diaper or an incontinence guard, which comprises an outer casing layer, an inner casing layer, and an absorbent pad enclosed between said inner and outer casing layers, at least one of the casing layers being manufactured from a thin elastic material which includes areas from which material has been removed while leaving coherent material parts in order to give different parts of the elastic material different elastic properties upon stretching thereof, the location of said areas on the article being chosen so as to give the article mutually different elastic properties in different parts thereof, said at least one of the inner and outer casing layers of elastic material including through holes and blind holes.

2. A disposable, absorbent article according to claim 1, wherein the inner casing layer is made of said thin elastic material and in use is intended to be closest to the body of the wearer, said thin elastic material having laminated thereto a non-woven material which includes through-holes and blind holes which coincide with the through holes and blind holes in the thin elastic material.

3. A disposable, absorbent article comprising an outer casing layer, an inner casing layer and an absorbent pad positioned between the inner and outer casing layers, at least one of the inner and outer casing layers being fabricated of an elastic memory material which is elastically stretchable from a contracted state to a stretched state and contractible after being stretched, said elastic memory material including areas from which material has been removed while leaving coherent material parts in order to give different parts of the material different elastic properties upon stretching said areas from which material has been removed includes through holes and blind holes, said blind holes being disposed in parts of said at least one of the inner and outer casing layers located outside said absorbent pad.

* * * * *